(12) United States Patent
Regazzoni (10) Patent No.: US 9,554,868 B2
(45) Date of Patent: Jan. 31, 2017

(54) METHOD AND APPARATUS FOR REDUCING MALALIGNMENT OF FRACTURED BONE FRAGMENTS

(75) Inventor: Luca Regazzoni, Basel (CH)

(73) Assignee: DePuy Synthes Products, Inc., Raynham, MA (US)

( * ) Notice: Subject to any disclaimer, the term of this patent is extended or adjusted under 35 U.S.C. 154(b) by 225 days.

(21) Appl. No.: 12/851,964

(22) Filed: Aug. 6, 2010

(65) Prior Publication Data

US 2011/0082367 A1      Apr. 7, 2011

Related U.S. Application Data

(60) Provisional application No. 61/232,170, filed on Aug. 7, 2009.

(51) Int. Cl.
*A61B 5/05* (2006.01)
*A61B 17/56* (2006.01)

(52) U.S. Cl.
CPC ............... *A61B 90/36* (2016.02); *A61B 34/20* (2016.02); *A61B 2017/565* (2013.01); *A61B 2090/364* (2016.02); *A61B 2090/367* (2016.02); *A61B 2090/3983* (2016.02)

(58) Field of Classification Search
USPC .......................................................... 606/58
See application file for complete search history.

(56) References Cited

U.S. PATENT DOCUMENTS 7,618,419 B2 * 11/2009 Lavallee ..................... 606/86 R
7,939,146 B2 *  5/2011 Borck et al. ................. 428/34.1
2006/0241388 A1   10/2006 Lavallee
2007/0043354 A1 *  2/2007 Koo et al. ....................... 606/58
2008/0208055 A1    8/2008 Bertram et al.
2009/0018437 A1 *  1/2009 Cooke .................... A61B 6/025
                                                              600/427
2012/0277581 A1 * 11/2012 Urushiya ................. A61B 6/12
                                                              600/427

FOREIGN PATENT DOCUMENTS

EP       1632181           3/2006
WO    WO 01/35842 A1       5/2001

OTHER PUBLICATIONS

Joskowicz et al. "FRACAS: A System for Computer-Aided Image-Guided Long Bone Fracture Surgery," Computer Aided Surgery, vol. 3, No. 6, pp. 271-288, 1999.*

* cited by examiner

*Primary Examiner* — Long V Le
*Assistant Examiner* — Kevin Pontius
(74) *Attorney, Agent, or Firm* — Baker & Hostetler LLP (57) ABSTRACT

A method and system for intraoperative, image-based reduction control for long bone shaft fracture treatment. The method includes preoperative steps of a) implanting markers into the proximal fragment and into the distal fragment of the broken bone, b) creating a 3D reference model of bone by taking a CT scan of the healthy bone, a CT scan of the broken bone and c) defining landmarks in the reference model based on the marker positions. The method further includes intraoperative steps of d) extracting the 3D position of the same landmarks from a series of 2D fluoroscopic images, using a reference object and e) comparing the positions the preoperatively defined landmarks and the positions of the intraoperatively extracted landmarks to calculate the malalignment of the fracture fragments.

17 Claims, 9 Drawing Sheets

COMPARING SAID SET OF MALALIGNMENT PARAMETERS (2000)
WITH A PRE-DEFINED SET OF ACCEPTABLE
MALALIGNMENT PARAMETERS (2001);

1902

DETERMINING EVENTUAL DEVIATIONS BETWEEN SAID SET OF
MALALIGNMENT PARAMETERS (2000) AND SAID PRE-DEFINED
SET OF ACCEPTABLE MALALIGNMENT PARAMETERS (2001);

1903

DECIDING WHETHER SAID DEVIATIONS ARE ACCEPTABLE
FOR THE SURGEON;

1904

FIXING SAID PROXIMAL AND DISTAL FRAGMENT (3,4) RELATIVE
TO EACH OTHER IF SAID DEVIATIONS ARE ACCEPTABLE
FOR THE SURGEON; OR

1905

IF SAID DEVIATIONS ARE NOT ACCEPTABLE FOR THE SURGEON;

1906

PERFORMING AT LEAST ONE REDUCTION STEP BY A SURGEON
OR APPARATUS AT THE FRACTURED LONG BONE (1) OF THE
PATIENT ON THE BASIS OF SAID SET OF
MALALIGNMENT PARAMETERS (2000);

1907

REPEAT STEPS 1802 TO 1810 AND STEPS 1901 TO 1906
UNTIL SAID DEVIATIONS ARE ACCEPTABLE FOR THE SURGEON.

METHOD AND APPARATUS FOR REDUCING MALALIGNMENT OF FRACTURED BONE FRAGMENTS

CROSS-REFERENCE TO RELATED APPLICATIONS

This application claims the benefit of U.S. Provisional Patent Application Ser. No. 61/232,170, filed Aug. 7, 2009, the disclosure of which is hereby incorporated by reference as if set forth in its entirety herein.

BACKGROUND

Many dislocated fractures of long bones, in particular of the lower extremities, are currently treated surgically (osteosynthesis). Every osteosynthesis typically includes preoperative, intraoperative and postoperative medical imaging. Preoperative and postoperative medical imaging is used for diagnosis and planning, and control, respectively. Intraoperative medical imaging, which is commonly achieved using a mobile fluoroscope, provides an optical feedback to control the manipulation of the fracture fragments, appropriate alignment and implant positioning.

In fractures of the lower limbs there are mainly two treatment options: closed reduction internal fixation (CRIF) and open reduction internal fixation (ORIF). In CRIF the reduction is carried out without direct exposure and direct visualization of the fracture. The only visual information about the fractured bone is provided by intraoperative fluoroscopy. In contrast, in ORIF, the fracture is exposed surgically by dissecting the overlaying soft tissues. Exposing the fracture, the surgeon can reduce it under direct vision controlling only the end result with the fluoroscope.

For the majority of shaft fractures of tibia and femur, CRIF using intramedullary nails is the treatment of choice. In other cases, for instance where closed reduction is impossible or in institutions where no image intensifier is available, ORIF is used. Closed reduction is preferred because it is less invasive, more respectful of soft tissues, it lowers the risk of greater blood loss, interferes less with the biology of fracture healing, and shows better cosmetic results. However, CRIF is technically more demanding for the surgeon and exposes both the patient and the medical staff to higher radiation doses.

Possible complications of fixing the femoral or tibial shaft include angular and/or rotational malalignment of the fracture fragments as well as incorrect restoration of the bone length. Such complications can cause false posture, or restricted movement and/or excessive strain on the patient's joint structures due to a significant change in the natural anatomical structure and biomechanics. In many cases, the above-mentioned complications could be avoided, if improved intraoperative visualization modalities were available.

A common intraoperative fluoroscope can visualize a circular region with a diameter of a maximum of 12-18 cm. Due to this limitation, the entire fractured bone can only be partially visualized. The shafts of tibia and femur have nearly no morphological or structural inhomogeneities. Consequently, the rotational alignment of the fracture fragments can not be readily determined from medical images containing the shaft alone. The visualization of a proper alignment of the fracture fragments indicates the desirability fo a representation of the whole bone including the shaft and the morphologically inhomogeneous epiphyses, from which the rotation of the fragments and the bone length can be determined What is therefore needed is an improved method and apparatus for properly positioning fractured bone fragments without having to use open reduction internal fixation.

SUMMARY

In accordance with one embodiment, a method is provided of reducing malalignment of fractured proximal and distal bone fragments of a fractured bone. The method includes the step of providing a first set of images of a contralateral bone, and a second set of images of the fractured bone. The contralateral bone is contralateral with respect to the fractured bone. The method further includes the step of obtaining a first 3D representation of the proximal bone fragment from the second set of images, a second 3D representation of the distal bone fragment from the second set of images, and a mirrored 3D representation of the contralateral bone from the first set of images. A first set of 3D coordinates of a first landmark is extracted from the first 3D representation, and a second set of 3D coordinates of a second landmark is extracted from the second 3D representation. The first set of 3D coordinates is transferred onto the mirrored 3D representation, and the second set of 3D coordinates is transferred onto the mirrored 3D representation. A relative position between the proximal bone fragment and the distal bone fragment is determined based on the transferred first and second sets of 3D coordinates.

BRIEF DESCRIPTION OF THE DRAWINGS

The foregoing summary, as well as the following detailed description of preferred embodiments of the application, will be better understood when read in conjunction with the appended drawings. For the purposes of illustrating the embodiments of the present application, there is shown in the drawings preferred embodiments. It should be understood, however, that the application is not limited to the precise arrangements and instrumentalities shown. In the drawings.

DETAILED DESCRIPTION

It should be appreciated that various embodiments described herein overcome possible complications of nailing of the femoral or tibial shaft, such as rotational malalignment of the fracture fragments as well as incorrect restoration of the bone length. Incorrect restoration of bone angles can also be achieved. In that regard, embodiments described herein can be used to establish and provide a reference set of digital data allowing the facilitation of a reduction procedure of a fractured long bone, the reduction of the number of medical images for the reduction procedure, and reducing costs of the reduction procedure.

Figure 1:
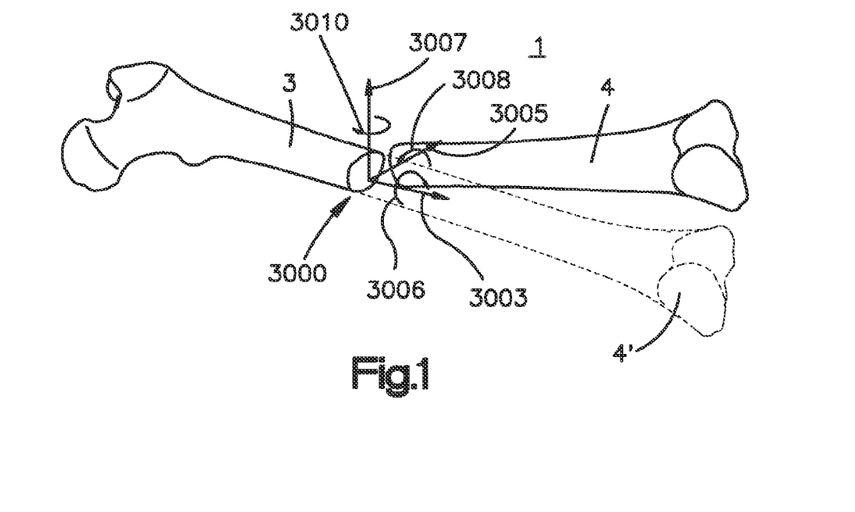
FIG. 1 is a schematic perspective view of a fractured long bone and of the virtually repositioned proximal and distal bone fragments of the fractured long bone.
Figure 2:
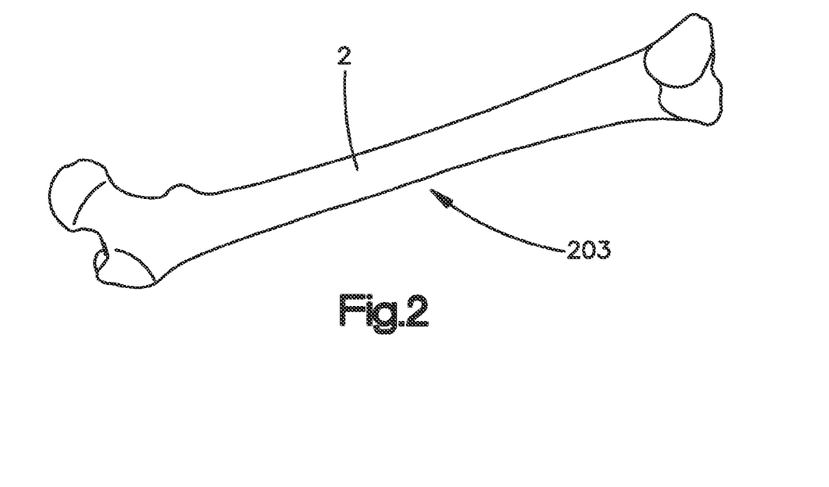
FIG. 2 is a schematic view of the 3D representation of a healthy contralateral bone used in accordance with one embodiment of a method of establishing a reference set of digital data.
Figure 3:
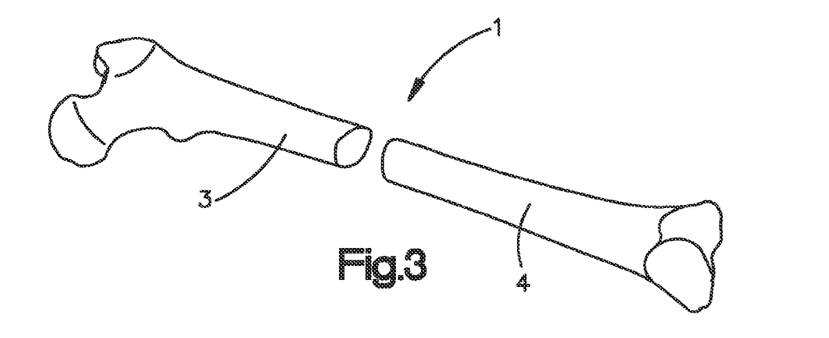
FIG. 3 is a schematic view of the 3D representation of a fractured long bone used in accordance with the embodiment associated with FIG. 2.

Referring initially to FIG. 1, a fractured long bone 1 is illustrated having a proximal bone fragment 3 separated from a distal bone fragment 4. The long bone 1 can include, but is not necessarily limited to, bones in the leg such as the femur and tibia, or bones of the arm such as the humerus, the ulna, and the radius. A virtual distal bone fragment 4' is indicated in a dotted line in a position after completing a malalignment reduction procedure as described herein. A system of coordinates 3000 which is fixed to the proximal bone fragment 3 can be used to determine a set of malalignment parameters. The coordinates 3000 include a longitudinal axis 3003 that extends generally parallel to the fractured bone when in a nonfractured state, a lateral axis 3005 that extends substantially perpendicular to the longitudinal axis 3003, and a transverse axis 3007 that extends substantially perpendicular to the longitudinal axis 3003 and the transverse axis 3005.

A clinical problem is the malalignment of the proximal and distal bone fragment 3, 4 after implantation of an intramedullary nail or other fixation apparatus. Intra-operatively, the reduction of the malalignment after intramedullary nailing can be performed with respect to a number of degrees of freedom. For instance, the distance between the bone fragments 3 and 4 along the longitudinal axis 3003 may be shortened or lengthened. Deviations in the angular direction 3006 about longitudinal axis 3003 may be adjusted via external or internal rotation of one or both bone fragments 3 and 4. Deviations in the angular direction 3008 about lateral axis 3005 may be adjusted via external or internal rotation of one or both bone fragments 3 and 4. Deviations in the angular direction 3010 about transverse axis 3007 may be adjusted via external or internal rotation of one or both bone fragments 3 and 4.

In accordance with one embodiment, the surgeon may desire that eventual deviations between the intra-operative set of malalignment parameters and a pre-defined set of acceptable malalignment parameters should not exceed a predetermined value. By way of example only, it might be desired that the distance between the bone fragments 3 and 4 along the longitudinal axis 3003 not excede approximately 1 cm. In another example, it may be desired that the rotational deviation about one or more of the angular directions, such as angular direction 3006, not excede between about 5° and about 20°. While the steps below are described in combination with one embodiment, it should be appreciated that deviations from the method, including but not limited to performing the steps in a different sequence than that described below, are contemplated.

FIGS. 2-7B illustrate schematically a possible embodiment where a reference set of digital data is established by using a first set 13 of landmarks 300, 301, and 302 in the proximal bone fragment 3, and a second set 15 of landmarks 400, 401, 402 in the distal bone fragment 4. In particular, radio opaque markers 300-302 and 400-402 are implanted, or otherwise affixed to or identified at the bone fragments 3 and 4 at desired locations. Unless otherwise specified, the terms "marker" and "landmark" are used synonymously herein to include an artificial landmark implanted in or on, or otherwise affixed to, a bone or bone fragment, and an anatomical landmark that can include a characteristic point or a two-dimensional or three-dimensional structure of a bone or bone fragment in case of a medical digital volume data set or of the surface of abone in case of a digital data set including the surface of the bone. Example anatomical landmarks can include the linea aspera and the trochanter minor. Example artificial markers are markers with defined geometry as known in the art, such as solid spheres or bone screws or the like, which can be fixed into or onto a bone or bone fragment. The artificial markers 13 can be made of magnesium, a magnesium alloy, or any other resorbable or non-resorbable, radio-opaque material.

Figure 7A:
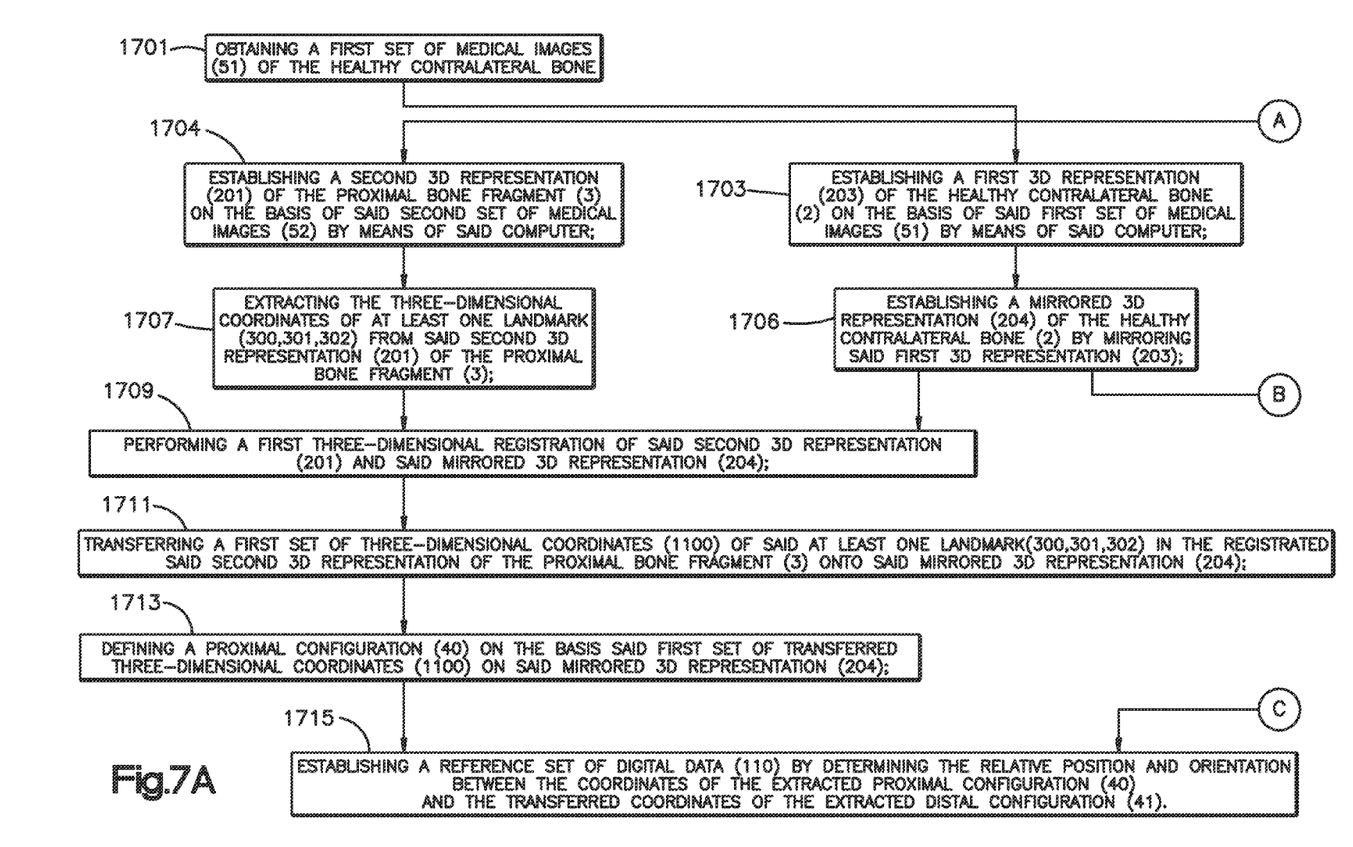
FIGS. 7A and 7B illustrate a flow chart with a sequence of steps performed in in accordance with the the method of establishing a reference set of digital data.

At step 1701, an imaging device, such as a CT scan, scans a healthy bone 2 that is the same bone, but contralateral to the fractured bone 1 to produce a first set of medical images 51 of the bone 2. At step 1702, an imaging device, such as a CT scan, scans the fractured bone 1 to produce a second set of medical images 52 of the fractured bone 1. As used herein, the term "CT scan" refers to a set of digital data which represents a series of medical images obtained with a computer tomography in a defined sequence. In another embodiment the medical imaging device is a medical X-ray device. In another embodiment the medical imaging device is a computer tomograph. In another embodiment the medical imaging device is not an ultrasound device, as medical images obtained using an ultrasound device can be less accurate than, for instance, a CT-scan. However, the use of an ultrasound device is not intended to fall outside the scope of the present invention unless otherwise specified.

It should be appreciated that the computer can be provided as any suitable pc or other computer or having a processor operating a stored program configured to perform the steps as describer herein. At step 1703, a first 3D representation 203 (e.g., a 3D model) of the healthy contralateral bone 2 can be created on a computer based on the first set of medical images 51 of the healthy contralateral bone 2. At step 1704, a second 3D representation 201 (e.g., a 3D model) of the proximal bone fragment 3 can be created on a computer based on the second set of medical images 52 of the proximal bone fragment 3. At step 1705, a third 3D representation 202 (e.g., a 3D model) of the distal bone fragment 4 can be created on a computer based on the second set of medical images 52 of the distal bone fragment 4.

It should be appreciated as described herein that the the creation of the 3D model of the healthy contralateral bone 2, of the 3D model of the proximal bone fragment 3 and of the 3D model of the distal bone fragment 4 need not be based on CT scans, and that any alternative structural image acquisition system capable of recording 3D images, or method to create 3D models based on one or several 2D images, or method of any kind to create 3D models can be used.

Figure 4:
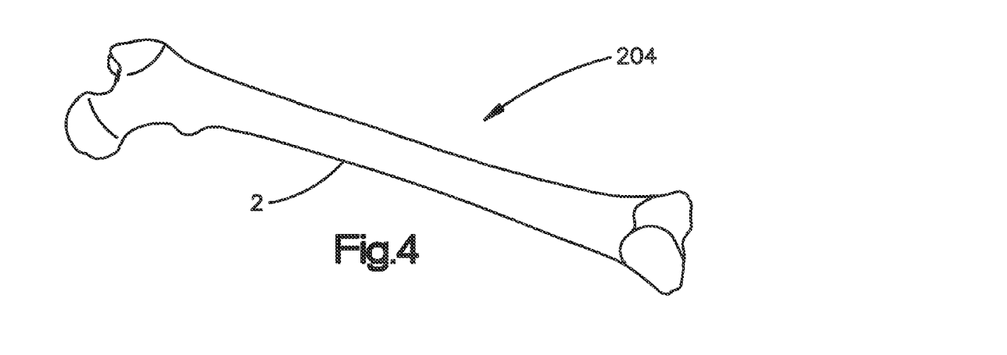
FIG. 4 is a schematic view of a mirrored 3D representation of the healthy contralateral bone of FIG. 2.

At step 1706, the 3D model 203 of the healthy contralateral bone 2 can be mirrored to produce a mirrored 3D representation 204 (i.e., a 3D model or image), so that the models 201-203 are of the same orientation, and the mirrored image 204 of the healthy contraleteral bone 2 can provide a reference for alignment reduction of the fractured bone 1. Alternatively, the 3D models 201 and 202 can be mirrored so that the 3D model 203 provides a reference for alignment reduction of the fractured bone 1.

Figure 5:
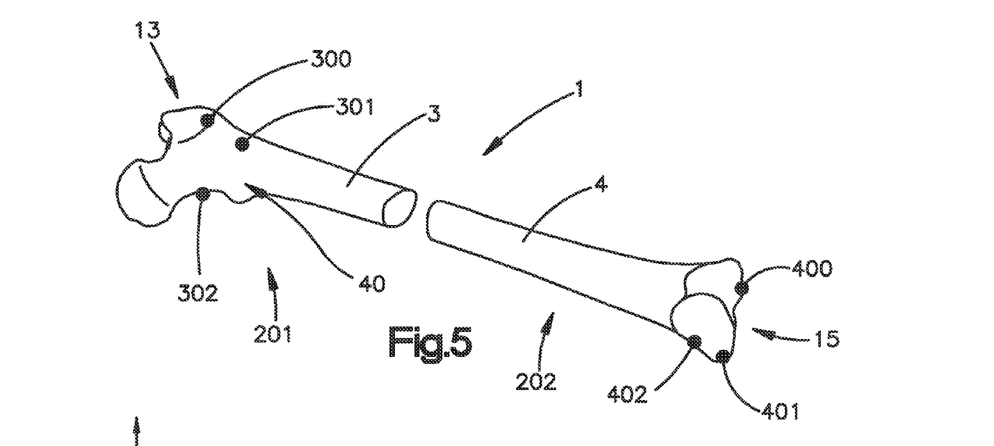
FIG. 5 is a schematic view of the 3D representation of the fractured long bone of FIG. 3 with defined landmarks.
Figure 6:
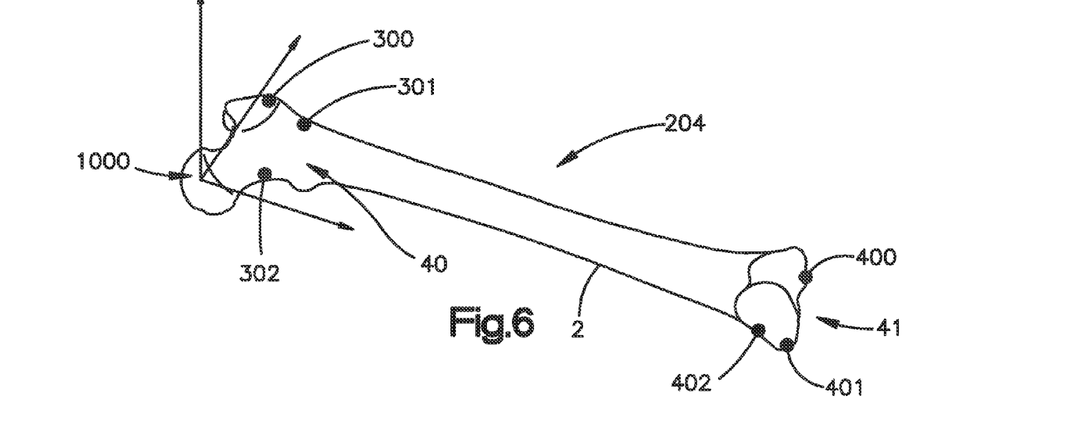
FIG. 6 is a schematic view of the mirrored 3D representation of the healthy contralateral bone of FIG. 4 with landmarks transferred from the 3D representation illustrated in FIG. 5.

At step 1707, the landmarks 300-302 are extracted from the 3D model of the proximal bone fragment 3 (which will be used to produce a proximal landmark configuration 40 on the mirrored image 204) and at step 1708, the landmarks 400-402 are extracted from the 3D model of the distal bone fragment 4 (which will be used to produce a distal landmark configuration 41 on the mirrored image 204). As used herein, the term "extract" refers to manually or automatically defining an object, structure, point or set of points in a digital dataset and marking or labeling its location within the digital dataset.

Figure 7B:
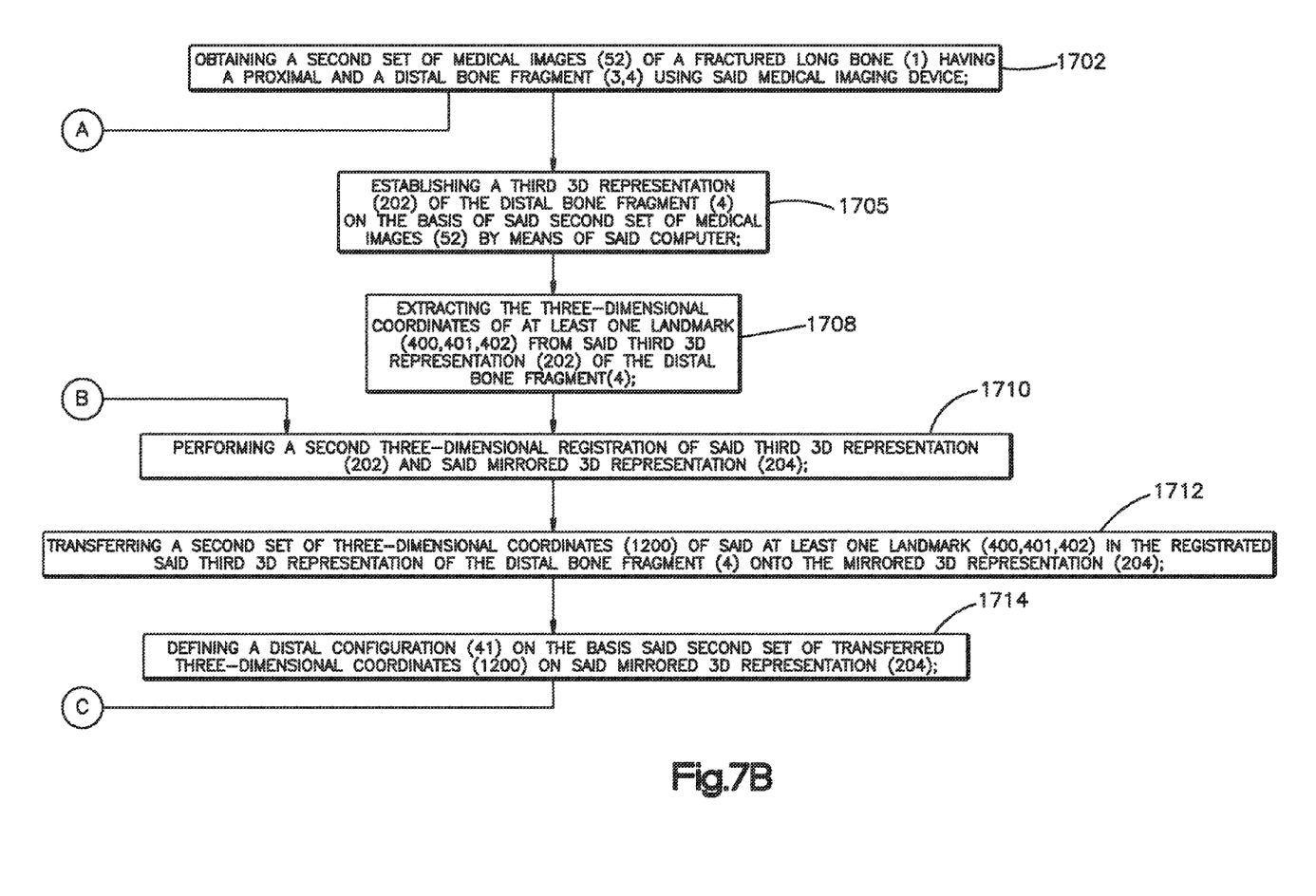

At step 1709, the 3D model of 201 of the proximal bone fragment 3 is 3-dimensionally registered with the mirrored 3-D model 204 of the healthy contralateral bone 2 at step 1709. As used here, the term "registering," "registration," and derivatives thereof refer to the accurate matching or superimposition of two or more images or 3D representations each defined by a respective set of digital data. At step 1711, three-dimensional coordinates 1100 of the extracted 3D landmarks 300-302 of the proximal bone fragment 3 are transferred onto the mirrored 3D model 204 of the healthy contralateral bone 2. Likewise, at step 1710, the 3D model of 202 of the distal bone fragment 4 is also 3-dimensionally registered with the mirrored 3-D model 204 of the healthy contralateral bone 2. At step 1712, three-dimensional coordinates 1200 of the extracted 3D landmarks 400-402 of the distal bone fragment 4 are transferred onto the mirrored 3D model 204 of the healthy contralateral bone 2. Thus, at steps 1713 and 1714, proximal and distal landmark configurations 40 and 41, respectively, are defined based on the transferred three-dimensional coordinates transferred at steps 1711 and 1712.

Once the proximal and distal landmark configurations 40 and 41 have been produced onto the mirrored model 204 of the healthy contralateral bone 2, the position and orientation of the proximal landmarks 300-302 of the proximal landmark configuration 40 on the mirrored image 204 of the healthy bone 2 relative to the position and orientation of the distal landmarks 400-402 of the distal landmark configuration 41 on the mirrored image 204 of the healthy bone 2 can be calculated at step 1715 to produce a reference set of digital data 110. The reference set of digital data 110 can then be used to manipulate bone fragments 3 and 4 until a sufficient level of malalignment reduction is achieved, as described in more detail below.

Referring now to FIGS. 8-11, one embodiment is illustrated for a method of determining a set of malalignment parameters for a fractured long bone 1 of a patient by using the reference set of digital data 110. While the steps below are described in combination with one embodiment, it should be appreciated that deviations from the method, including but not limited to performing the steps in a different sequence than that described below, are contemplated.

Figure 8:
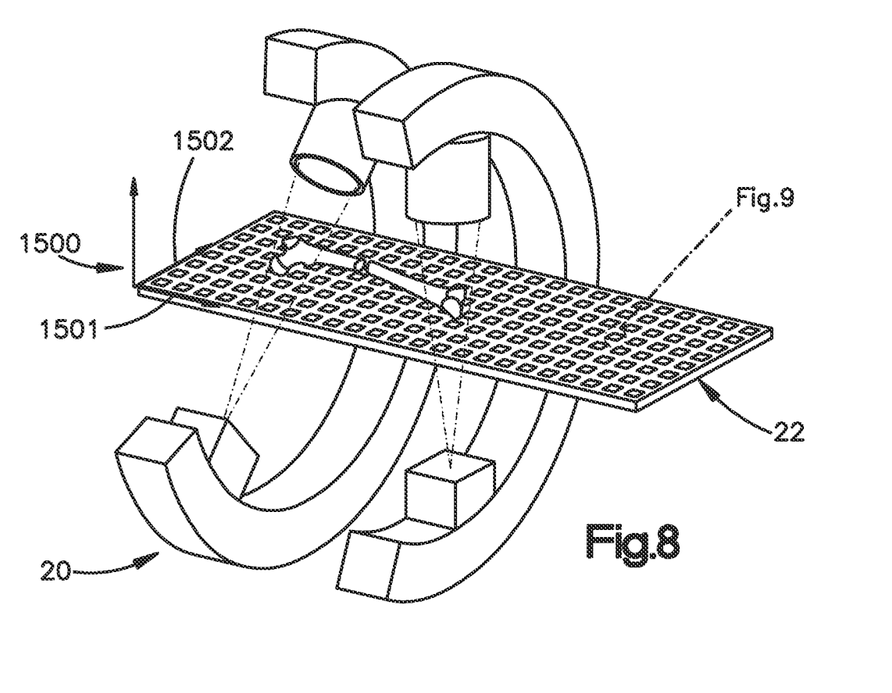
FIG. 8 is a schematic view of an embodiment of the method of intra-operatively determining a set of malalignment parameters for a fractured long bone of a patient according to the invention.
Figure 10:
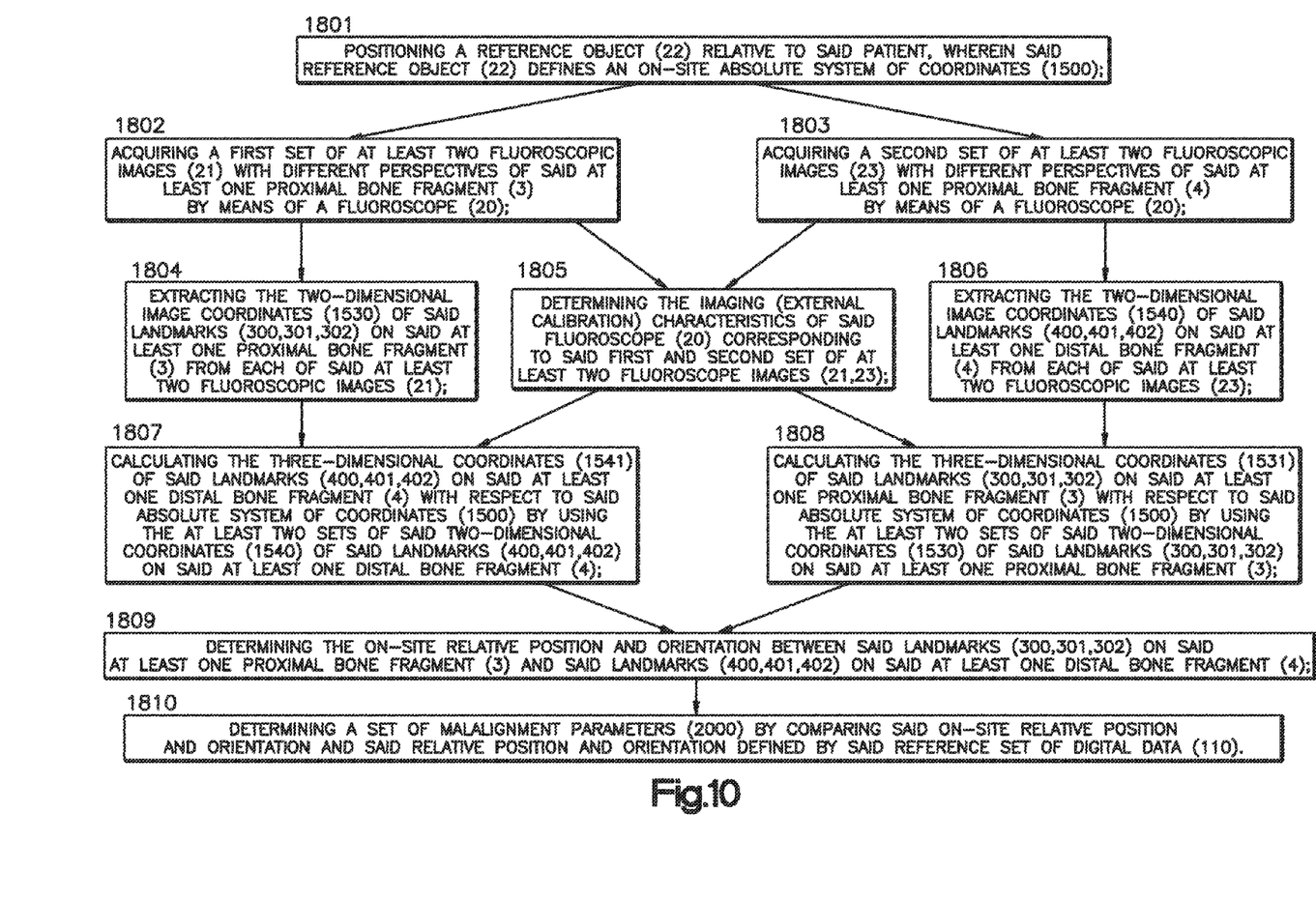
FIG. 10 is a flow chart with a sequence of steps performed in an embodiment of the method of intra-operatively determining a set of malalignment parameters for a fractured long bone of a patient according to the invention.

At step 1801, a reference object 22 is positioned relative to a patient having a broken bone. The reference object 22 defines an on-site absolute system of coordinates 1500. At step 1802, at least two (for instance three) fluoroscopic images 21 of the proximal bone fragment 3 are acquired from different perspectives to produce a plurality of 2D image coordinates 1530 of the landmarks 300-302. At step 1803, and at least two (for instance three) fluoroscopic images 23 of the distal fragment 4 are acquired from different perspectives to produce a plurality of 2D image coordinates 1540 of the landmarks 400-402. It should be appreciated that in steps 1801 and 1802, any suitable number of fluoroscopic images from different perspectives may be taken to produce a sufficiently accurate representation of the position of the landmarks 300-302 and 400-402. The acquisition of the first and the second set of at least two fluoroscopic images can be performed with different perspectives of each of the proximal bone fragment and the distal bone fragment. For instance, the different perspectives may be minimum +20° or −20° with respect to an caudio-cranial axis of the patient. The different perspectives may be maximum +40° or −40° with respect to an caudio-cranial axis of the patient (typically: +30° or −30°).

At step 1804, the 2D image coordinates 1530 of the landmarks 300-302 from the fluoroscopic images 21 of the proximal bone fragment 3 are extracted. At step 1806, the 2D image coordinates 1540 of the landmarks 400-402 from the fluoroscopic images 23 of the distal bone fragment 4 are extracted.

Once the imaging (e.g., external calibration) characteristics of the fluoroscope 20 corresponding to the flurosocpic images 21 and 23 are determined at step 1805, calculations of the coordinates is performed. For instance at step 1807, the 3D coordinates of the proximal landmarks 300-302 are calculated, for instance, by triangulating the coordinates of the landmarks 300-302 from the extracted image coordinates 1530 of the landmarks 300-302 of the proximal bone fragment 3. At step 1808, the 3D coordinates of the distal landmarks 400-402 are calculated, for instance, by triangulating the coordinates of the landmarks 400-402 from the extracted image coordinates 1540 of the landmarks 400-402 of the distal bone fragment 4.

At step 1809, the relative position and orientation of the 3D landmark configurations determined at steps 1807 and 1808 are calculated. At step 1810, the fragment malalignment of the fractured bone 1 is determined by comparing the geometrical relationship of the landmark configurations on the mirrored according to step 1715 and the geometrical relationship of the landmark configuration according to step 1809. If the malalignment determined at step 1810 is outside of a surgeon's desired tolerances, the relative position of the proximal and distal bone fragments 3 and 4 can be externally or internally adjusted, and the above method steps can be repeated until the malalignment determined at step 1810 is as desired, as described in more detail below.

It should be appreciated at steps 1802-1803 and 1804 and 1806, The 3D reconstruction of the landmarks from intraoperative fluoroscopic images in accordance with one embodiment uses three images of the same region containing the landmarks. The three images are preferably acquired from different perspectives. The 3D reconstruction algorithm may be subdivided into three steps:

i. Internal and external calibration of the intraoperative fluoroscope.

ii. Extraction of the 2D landmarks, which are 3D reconstructed, from the 2D fluoroscopic images.

iii. 3D reconstruction of the previously extracted 2D landmarks through triangulation or similar techniques. In the present method, the use of an absolutely coded reference plate as a reference object 22, e.g. as specified in EP-A 1 632 181 MESSMER, which is placed near the fractured bone 1 and which is partly visible in all fluoroscopic images is possible. The plate has imprinted markings 1510 (FIG. 9) on it coding for the position within the plate.

Figure 9:
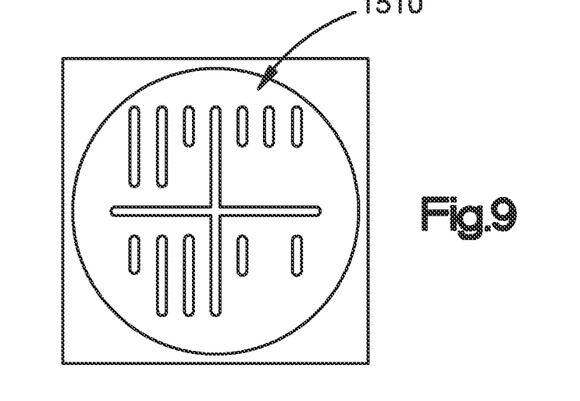
FIG. 9 is a magnified view of the of—FIG. 9—region of FIG. 8.

The plate's geometry, in particular the spacing between the markings 1510, is known. Using the plate 22 facilitates the calibration of the fluoroscope 20 and makes it possible to assess the relative position and orientation between the 3D reconstructed, proximal landmark configuration and distal landmark configuration. In fact, the markings 1510 on the plate 22 can provide a set of point correspondences between an image containing them and the physical plate itself. The knowledge of these point correspondences makes an accurate, robust and easy-to-implement camera calibration possible. Furthermore, to be comparable, the 3D reconstructed proximal landmarks are be described in the same coordinate system as the 3D reconstructed distal landmarks. Performing the 3D reconstruction without the help of any reference object, the proximal and the distal landmarks would be described in distinct coordinate systems. Using the reference plate, an absolute coordinate system 1500 can be defined. In this coordinate system, the positions and orientation of the two landmarks configurations can be described and compared.

Using a flat (i.e. 2D) reference object 22 as the absolutely coded reference plate imposes to take three fluoroscopic images to calibrate the fluoroscope. Using a 3D reference object, the number of images could be reduced to one image for the camera calibration and to two images for the 3D reconstruction step. A 2D reference object may be desired because it can be placed underneath the patient or even be completely integrated in an operating table without being cumbersome to the surgeon. It will be understood that substituting the absolutely coded reference plate with another reference object of any kind, implicating changes in the computational algorithms and in the workflow of the method, including the number of fluoroscopic images, for instance to 3D reconstruct the 3D position of landmarks from intraoperative 2D images, is contemplated.

The described embodiments allow for more than only the relative position and orientation of bone fragments to be assessed. In fact, the method can also be used to extract the 3D position and orientation of any object, such as a surgical object, based on 2D images when more than one landmark on the object is visible and extractable in several 2D images, the coded reference plate is visible in the same images, and a 3D reference model of the (surgical) object is available For this application, the procedure would basically include performing steps 1801-1804 and 1806 (and optionally step 1805) described above with respect to FIG. 10 to extract the 3D landmarks from several images, to extract the same landmarks from the 3D reference model and to match the reference landmarks with the 3D reconstructed landmarks.

Figure 11:
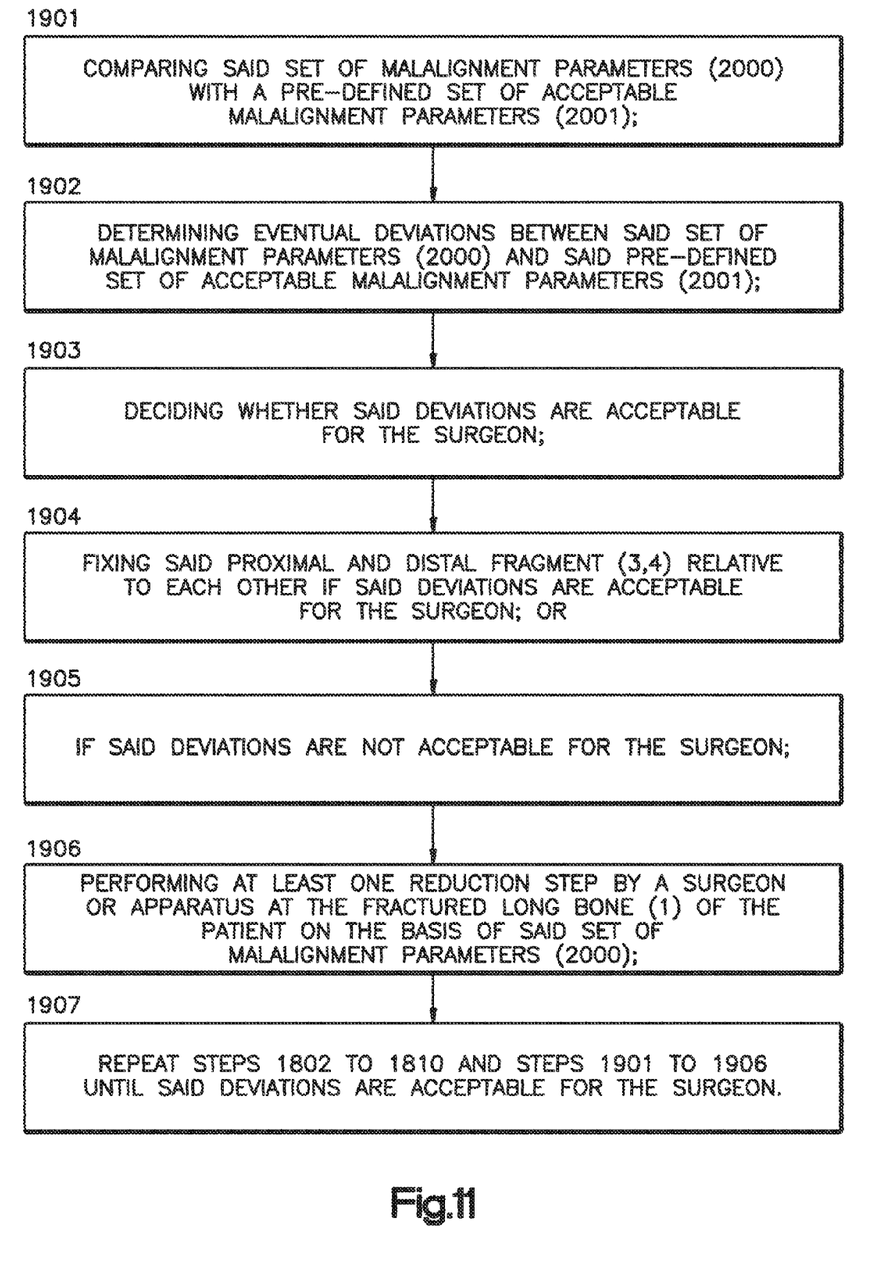
FIG. 11 is a flow chart with a sequence of steps performed in an embodiment of the method of performing a reduction of a fractured long bone by using the set of malalignment parameters.

FIG. 11 is a flow chart with a sequence of steps performed in an embodiment of the method of performing a reduction of a fractured long bone 1 by using the set of malalignment parameters. The method of performing a reduction of a fractured long bone 1 includes steps described below in combination with one embodiment, it being appreciated that deviations from the method, including but not limited to performing the steps in a difference sequence than that described below, are contemplated.

The method includes step 1901 of comparing the set of malalignment parameters 2000 with a predetermined set of acceptable malalignment parameters 2001. Next, at step 1902, eventual deviations between the set of malalignment parameters 2000 and the pre-defined set of acceptable malalignment parameters 2001 are determined. At step 1903, it is decided (for instance by the surgeon) whether the deviations are acceptable. At step 1904 the proximal and distal fragments (3, 4) are fixed relative to each other if the deviations are acceptable If the deviations are not acceptable at step 1905, then a reduction step is performed at step 1906 on the basis of the set of malalignment parameters. For instance, the reduction step can reduce the malalignment deviation deemed unacceptable at step 1905. Steps 1802-1810 and steps 1901-1906 can be repeated until the deviations are deemed acceptable (for instance to the surgeon).

Referring now to FIGS. 12-15, another method of establishing a reference set of digital data is illustrated. It should be appreciated that deviations from the method, including but not limited to performing the steps in a difference sequence than that described below, are contemplated.

Figure 12:
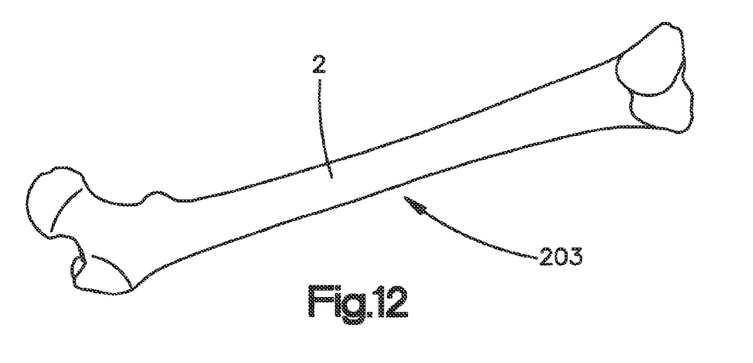
FIG. 12 is a schematic view of the 3D representation of the healthy contralateral bone used in an embodiment of the method of establishing a reference set of digital data according to the invention.
Figure 13:
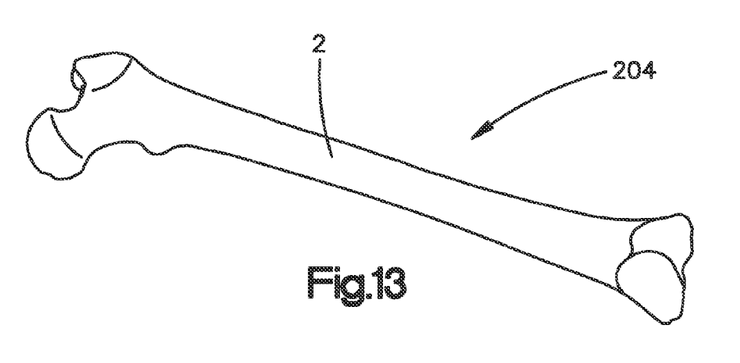
FIG. 13 is a schematic view of the mirrored 3D representation of the healthy contralateral bone of FIG. 12.
Figure 15:
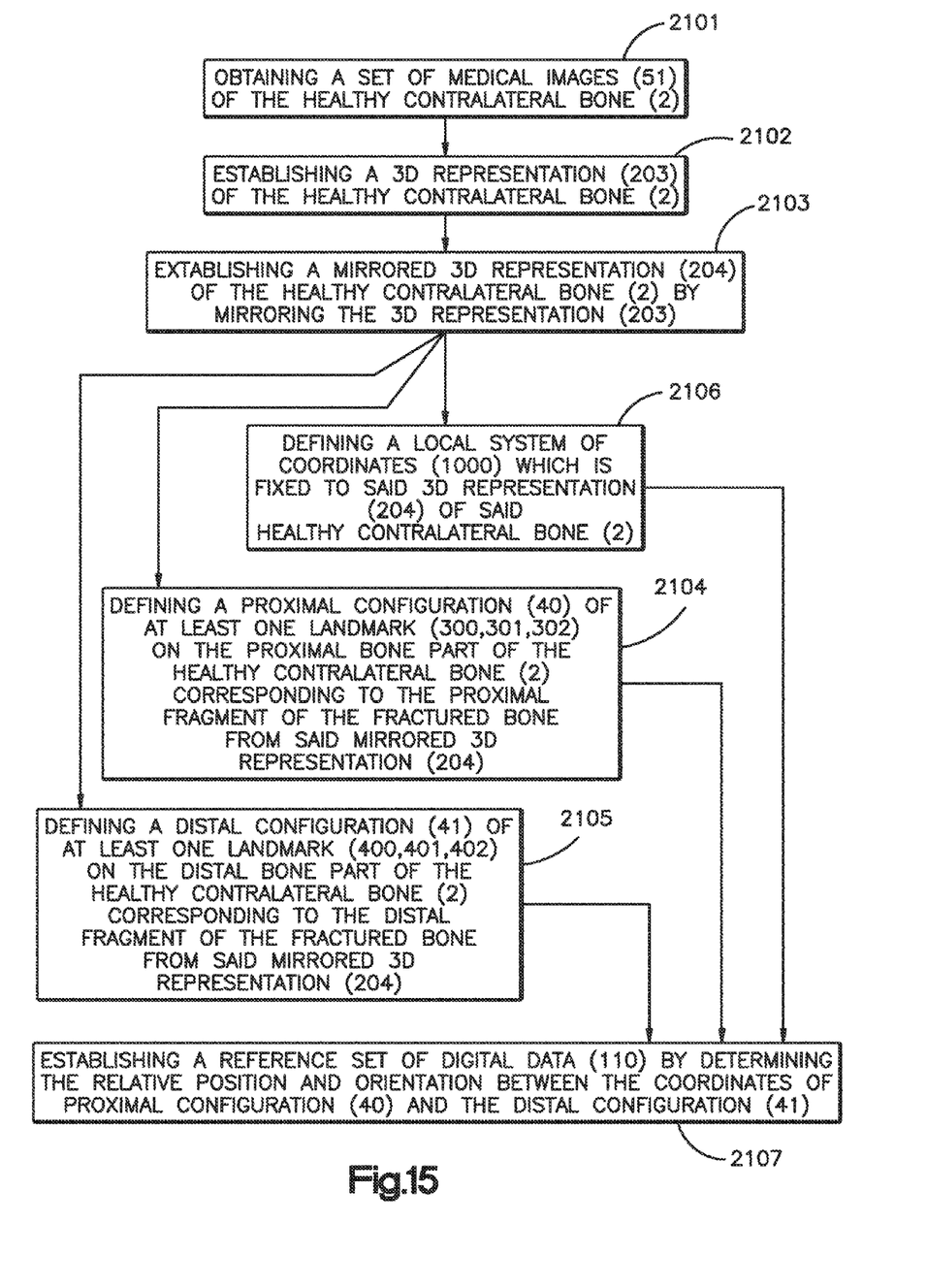
FIG. 15 is a flow chart with a sequence of steps performed in the embodiment of the method of establishing a reference set of digital data.

The method includes step 2101 of obtaining a first set of medical images 51 of the healthy contralateral bone 2. The set of medical images 51 can be provided as a plurality of two-dimensional images as described above, or can be provided as a three-dimensional image. At step 2102, if a plurality of two-dimensional images were taken at step 2101, a three-dimensional representation 203 of the healthy contralateral bone 2 is provided based on the two-dimensional images. At step 2103, the three-dimensional image is mirrored to provide a mirrored three-dimensional image 204 of the healthy contralateral bone 2 so that a three-dimensional image of a fractured bone 1 contralateral with respect to the healthy bone 2 can eventually be registered with the mirrored image 204.

Figure 14:
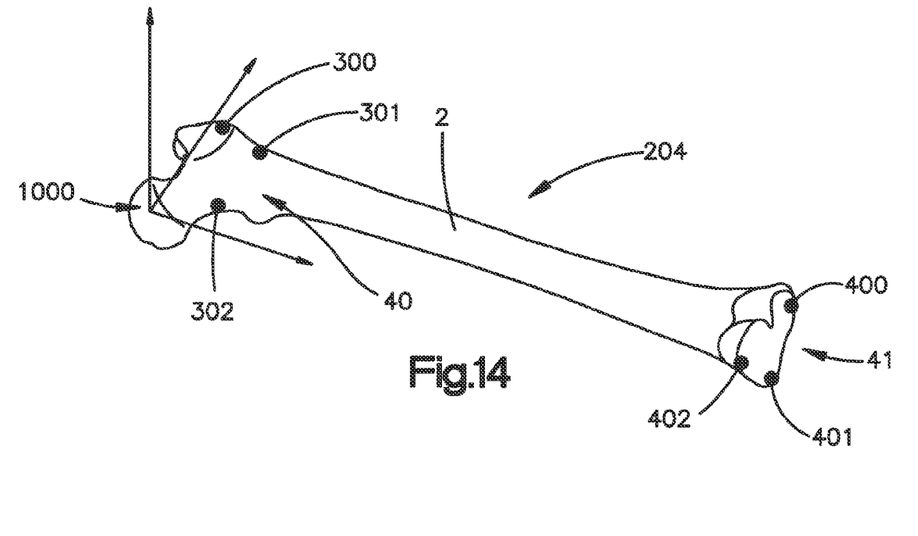
FIG. 14 is a schematic view of the mirrored 3D representation of the healthy contralateral bone of FIG. 12 with defined landmarks.

Next, at step 2104 the proximal configuration 40 of at least one landmark (for instance landmarks 300-302) is defined on the mirrored image 204 of the healthy contralateral bone 2, corresponding to the proximal fragment of the fractured bone. At step 2105, the distal configuration 41 of at least one landmark (for instance landmarks 400-402) is defined on the mirrored image 204 of the healthy contralateral bone 2, corresponding to the distal fragment of the fractured bone. In this regard while a plurality of landmarks are defined on the mirrored image 204 corresponding to each fragment of the fractured bone as illustrated, it should be appreciated that a malalignment reduction of the fractured bone can be achieved even when only one landmark of each fractured bone fragment is defined on the mirrored image (for instance, longitudinal displacement of the bone fragments).

At step 2106, a local system of coordinates can be fixed to the 3D representation of the mirrored image 204 of the healthy contralateral bone 2. Finally, at step 2107, a reference set of digital data 110 can be established by determining the relative position and orientation between the coordinates of the landmarks 300-302 of the proximal configuration and the corresponding landmarks 400-402 of the distal configuration 41. The relative position and orientation calculated at step 2107 can be used to determine and to reduce, if desired, the malalignment parameters of the fractured bone.

It should be appreciated that various embodiments described herein overcome possible complications of nailing of the femoral or tibial shaft, such as rotational malalignment of the fracture fragments as well as incorrect restoration of the bone length. Incorrect restoration of bone angles can also be achieved, to the extent that they cannot be readily by visual inspection or direct three-dimensional imaging.

Thus, embodiments described herein can be used to establish and provide a reference set of digital data allowing the facilitation of a reduction procedure of a fractured long bone, the reduction of the number of medical images for the reduction procedure, and reducing costs of the reduction procedure.

One method of establishing a reference set of digital data on the basis of which a set of malalignment parameters for a shaft fracture treatment of a long bone can be determined, comprises the steps of a) obtaining a first set of medical images of the healthy contralateral bone using a medical imaging device, b) obtaining a second set of medical images of a fractured long bone having a proximal and a distal bone fragment using the medical imaging device; c) establishing a first 3D representation of the healthy contralateral bone on the basis of the first set of medical images using the computer; d) establishing a second 3D representation of the proximal bone fragment on the basis of the second set of medical images on the computer; e) establishing a third 3D representation of the distal bone fragment on the basis of the second set of medical images on the computer; e) orientating the contralateral healthy bone in the same general orientation as the fractured bone by, for instance, mirroring the first 3D representation; f) extracting the three-dimensional coordinates of at least one landmark from the second 3D representation of the proximal bone fragment; g) extracting the three-dimensional coordinates of at least one landmark from the third 3D representation of the distal bone fragment; h) performing a first three-dimensional registration of the second 3D representation and the mirrored 3D representation; i) transferring a first set of three-dimensional coordinates of the at least one landmark on the proximal bone fragment onto the mirrored 3D representation; j) performing a second three-dimensional registration of the third 3D representation and the mirrored 3D representation; k) transferring a second set of three-dimensional coordinates of the at least one landmark on the distal bone fragment onto the mirrored 3D representation; l) defining a proximal configuration on the basis of the first set of transferred threedimensional coordinates on the mirrored 3D representation; m) defining a distal configuration on the basis the second set of transferred threedimensional coordinates on the mirrored 3D representation; and n) establishing a reference set of digital data by determining the relative position and orientation between the coordinates of the extracted proximal configuration and the transferred coordinates of the extracted distal configuration.

Thereby, the transferred first set of three-dimensional coordinates of the at least one landmark onto the mirrored 3D representation is a set of three-dimensional coordinates of the at least one landmark in the registrated second representation of the proximal bone fragment, and the transferred second set of three-dimensional coordinates of the at least one landmark onto the mirrored 3D representation is a set of three-dimensional coordinates of the at least one landmark in the registrated third representation of the proximal bone fragment.

The landmarks can be anatomical landmarks (e.g., a characteristic point or a two-, or three dimensional structure of a bone in case of a medical digital volume data set or of the surface of a bone in case of a digital data set including the surface of the bone only) such as the linea aspera and the trochanter minor and/or artificial markers (e.g., markers with defined geometry as known in the art, which can be fixed into or onto a bone, such as a solid sphere a bone screw). For instance a combined use of anatomical landmarks and artificial markers can be advantageous if not enough suitable anatomical landmarks can be specified as e.g. in a bone fragment of the diaphysis of the fractured long bone. The artificial markers preferably consist of a resorbable radioopaque material, which can be formed from magnesium or a resorbable magnesium alloy, which can contain at least 75% by weight magnesium.

In another embodiment the method further includes the steps of defining a proximal configuration of at least one landmark on the proximal bone part of the healthy contralateral bone corresponding to the proximal bone fragment of the fractured bone from the mirrored 3D representation; and defining a distal configuration of at least one landmark on the distal bone part of the healthy contralateral bone corresponding to the distal bone fragment of the fractured bone from the mirrored 3D representation.

In another embodiment the method further includes the steps of establishing a first set of digital data representing the first set of medical images on a computer; and establishing a second set of digital data representing the second set of medical images from the computer.

In another embodiment the mirrored 3D representation is used as a reference to establish a local system of coordinates. A local system of coordinates can be intraoperatively referenced to an on-site absolute system of coordinates.

In another embodiment the method includes the step of storing the reference set of digital data on a digital data carrier.

In another embodiment a method of establishing a reference set of digital data on the basis of which a set of malalignment parameters for a shaft fracture treatment of a long bone can be determined includes the steps of a) obtaining a set of medical images of the healthy contralateral bone using a medical imaging device; b) establishing a 3D representation of the healthy contralateral bone; c) establishing a mirrored 3D representation of the healthy contralateral bone by mirroring the 3D representation; d) defining a proximal configuration of at least one landmark on the proximal bone part of the healthy contralateral bone corresponding to the proximal bone fragment of the fractured bone from the mirrored 3D representation; e) defining a distal configuration of at least one landmark on the distal bone part of the healthy contralateral bone corresponding to the distal bone fragment of the fractured bone from the mirrored 3D representation; and f) establishing a reference set of digital data by determining the relative position and orientation between the coordinates of the proximal configuration and of the distal configuration.

In another embodiment the landmarks are provided as anatomical landmarks. In another embodiment the method comprises the further step of storing the reference set of digital data on a digital data carrier. In another embodiment the mirrored 3D representation is used as a reference to establish a reference system of coordinates.

Certain embodiments as described herein can establish and provide a method of determining a set of malalignment parameters for a fractured long bone of a patient by using the reference set of digital data. A method of determining a set of malalignment parameters for a fractured long bone of a patient by using the reference set of digital data includes the steps of a) positioning a reference object relative to the patient, wherein the reference object defines an on-site absolute system of coordinates; b) acquiring a first set of at least two fluoroscopic images with different perspectives of the at least one proximal bone fragment using a fluoroscope; c) acquiring a second set of at least two fluoroscopic images with different perspectives of the at least one distal bone fragment using the fluoroscope; d) determining the imaging characteristics of the fluoroscope corresponding to the first and second set of fluoroscopic images; e) extracting the two-dimensional image coordinates of the landmarks on the at least one proximal bone fragment from each of the at least two fluoroscopic images; f) extracting the two-dimensional image coordinates of the landmarks on the at least one distal bone fragment from each of the at least two fluoroscopic images; g) calculating the three-dimensional coordinates of the landmarks on the at least one proximal bone fragment with respect to the absolute system of coordinates by using the at least two sets of the two-dimensional coordinates of the landmarks on the at least one proximal bone fragment; h) calculating the three-dimensional coordinates of the landmarks on the at least one distal bone fragment with respect to the absolute system of coordinates by using the at least two sets of the two-dimensional coordinates of the landmarks on the at least one distal bone fragment; i) determining the on-site relative position and orientation between the landmarks on the at least one proximal bone fragment and the landmarks on the at least one distal bone fragment; and j) determining a set of malalignment parameters by comparing the on-site relative position and orientation and the relative position and orientation defined by the reference set of digital data.

The imaging characteristics can include the external fixation of the fluoroscope. The imaging characteristics include the determination of the position and orientation of the X-ray source. Calibrating the fluoroscope is used herein to refer to determining the position and orientation of the X-ray source, as well as determining the imaging qualities of the fluoroscope. In another embodiment the on-site system of coordinates has at least a first and a second axis of coordinates which are metrically scaled.

Another embodiment establishes and provides a method of performing a reduction of a fractured long bone by using the set of malalignment parameters. A method of performing a reduction of a fractured long bone by using the set of malalignment parameters includes the steps of a) comparing the set of malalignment parameters with a pre-defined set of acceptable malalignment parameters; b) determining eventual deviations between the set of malalignment parameters and the pre-defined set of acceptable malalignment parameters; c) deciding whether the deviations are acceptable; d) fixing the proximal and distal fragment relative to each other if the deviations are acceptable; or if the deviations are not acceptable, e) performing at least one reduction step by a surgeon or apparatus at the fractured long bone of the patient on the basis of the set of malalignment parameters; and f) repeating certain of the above steps determining a set of malalignment parameters and all steps of the method of performing a reduction of a fractured long bone until the deviations are acceptable for the surgeon.

Another embodiment provides a method of determining calibration parameters of a fluoroscope which is used intraoperatively for determining a set of malalignment parameters for a fractured long bone of a patient and for performing a reduction of a fractured long bone. A method of determining calibration parameters of a fluoroscope which is used intraoperatively for determining a set of malalignment parameters for a fractured long bone of a patient and for performing a reduction of a fractured long bone includes the steps of positioning a reference object which defines an on-site absolute system of coordinates; acquiring a set of fluoroscopic images with different perspectives of the reference object; acquiring a second set of fluoroscopic images with different perspectives of the at least one distal bone fragment using the fluoroscope; and determining the intrinsic calibration parameters of the fluoroscope using the set of fluoroscopic images.

The Intrinsic calibration parameters can be used to specify the imaging characteristics (internal calibration). In another embodiment the method further comprises the step of: determining of the position and orientation of the fluoroscope by using the intrinsic calibration parameters. The extrinsic calibration parameters specify the position and orientation of the fluoroscope.

Using the reference set of digital data and assisted by a computer, the surgeon can intraoperatively determine the relative position and orientation of the fragments of a fractured long bone and to compare their malalignment with the healthy contralateral bone.

A system can be provided for performing the reduction of a fractured long bone, including a suitable intraoperative fluoroscope, a medical imaging device configured to produce preoperative CT scans of the healthy as well as the fractured long bone, a reference object which is at least partly visible in the fluoroscopic images, a computer or other suitable processer operating a stored program to perform one or more, up to all, of the method steps described above. In certain embodiments, the system can include artificial markers which can be implanted in each fragment and can be easily seen and the position of which can be automatically determined from x-ray based visualizations.

The acquisition of a first and a second set of at least two fluoroscopic images can be performed with different perspectives of each of the proximal bone fragment and the distal bone fragment using a fluoroscope. For instance, the different perspectives are minimum +20° or −20° with respect to an caudio-cranial axis of the patient. The different perspectives are maximum +40° or −40° with respect to an caudio-cranial axis of the patient (typically: +30° or −30°).

Although embodiments and their advantages have been described in detail, it should be understood that various changes, substitutions, and alterations can be made herein without departing from the spirit and scope of the invention, for instance as defined by the appended claims. In this regard, it should be appreciated that while certain methods are described above with respect to various method steps, the methods are not intended to be limited to the particular steps described, and the steps described can be performed in different orders than the order described. Moreover, the scope of the present application is not intended to be limited to the particular embodiments of the process, machine, manufacture, composition of matter, methods and steps described in the specification. As one of ordinary skill in the art will readily appreciate from the disclosure of the present invention, processes, machines, manufacture, composition of matter, methods, or steps, presently existing or later to be developed that perform substantially the same function or achieve substantially the same result as the corresponding embodiments described herein may be utilized according to the present invention. It will be appreciated by those skilled in the art that various modifications and alterations of the invention can be made without departing from the broad scope of the appended claims. Some of these have been discussed above and others will be apparent to those skilled in the art.

The invention claimed is:

1. A method of reducing malalignment of a fractured bone that defines a proximal bone fragment and a distal bone fragment that is separated from the proximal bone fragment by a fracture, the method comprising:

identifying at least one first anatomical landmark on the proximal bone fragment, and identifying at least one second anatomical landmark on the distal bone fragment;

providing a first set of images of a bone that is contralateral with respect to the fractured bone, and a second set of images of the fractured bone including the first and second anatomical landmarks;

obtaining a first 3D representation of the proximal bone fragment and the at least one first anatomical landmark from the second set of images, a second 3D representation of the distal bone fragment and the at least one second anatomical landmark from the second set of images, and a mirrored 3D representation of the contralateral bone from the first set of images;

extracting a first set of 3D coordinates of the at least one first anatomical landmark from the first 3D representation, and a second set of 3D coordinates of the at least one second anatomical landmark from the second 3D representation;

transferring the first set of 3D coordinates onto the mirrored 3D representation, and transferring the second set of 3D coordinates onto the mirrored 3D representation;

determining a planned relative position between the proximal bone fragment and the distal bone fragment based on a position of the transferred first set of 3D coordinates relative to the transferred second set of 3D coordinates;

after the determining step, reducing the fractured bone by moving at least one of the proximal bone fragment and the distal bone fragment relative to the other of the proximal bone fragment and the distal bone fragment;

ascertaining an on-site actual relative position between the identified at least one first anatomical landmark of the proximal bone fragment and the identified at least one second anatomical landmark of the distal bone fragment by (a) positioning the proximal and the distal bone fragments on an upper, flat surface of a reference plate, the upper surface having a plurality of adjacent markings separated by a known distance between adjacent markings; (b) acquiring a first-moved set of at least two fluoroscopic images with different perspectives of the proximal bone fragment, and a second-moved set of at least two fluoroscopic images with different perspectives of the distal bone fragment; (c) extracting a first moved-set of 2D image coordinates of the first anatomical landmark on the proximal bone fragment from the first-moved set of at least two fluoroscopic images, and extracting a second-moved set of 2D image coordinates of the second anatomical landmark on the distal bone fragment from the second-moved set of at least two fluoroscopic images; (d) calculating a first moved-set of 3D coordinates of the first anatomical landmark on the proximal bone fragment and a second moved-set of 3D coordinates of the second anatomical landmark on the distal bone fragment with respect to the plurality of adjacent markings on the reference plate by using the first and second moved-sets of 2D image coordinates of the first and second anatomical landmarks on the proximal bone fragment and the distal bone fragment, respectively; and (e) determining the on-site actual relative position between the first anatomical landmark on the proximal bone fragment and the second anatomical landmark on the distal bone fragment after the reducing step based upon the calculated first moved-set of 3D coordinates of the first anatomical landmark on the proximal bone fragment and the calculated second moved-set of 3D coordinates of the second anatomical landmark on the distal bone fragment; and calculating a set of malalignment parameters by comparing the on-site actual relative position to the planned relative position.

2. The method of claim 1, further comprising:

performing a first 3D registration of the first 3D representation and the mirrored 3D representation prior to the transfer of the first set of 3D coordinates onto the mirrored 3D representation;

performing a second 3D registration of the second 3D representation and the mirrored 3D representation prior to the transfer of the second set of 3D coordinates onto the mirrored 3D representation.

3. The method of claim 1 further comprising:

defining a proximal configuration of at least one anatomical landmark on a proximal bone part of the contralateral bone corresponding to the proximal bone fragment of the fractured bone from the mirrored 3D representation; and defining a distal configuration of at least one anatomical landmark on a distal bone part of the contralateral bone corresponding to the distal bone fragment of the fractured bone from the mirrored 3D representation.

4. The method of claim 1, wherein the step of providing the first set of images is performed using a medical imaging device.

5. The method of claim 4, wherein the medical imaging device is a computer tomograph or a medical X-ray device.

6. The method of claims 1, wherein the mirrored 3D representation is used as a reference to establish a local system of coordinates.

7. The method of claim 1, further comprising reducing the fractured bone in accordance with the set of malalignment parameters.

8. The method of claim 7, wherein the reducing step further comprises:

comparing the set of malalignment parameters with a pre-defined set of acceptable malalignment parameters;

determining deviations between the set of malalignment parameters and the pre-defined set of acceptable malalignment parameters;

deciding whether the deviations are acceptable; and fixing the proximal and distal fragment relative to each other if the deviations are acceptable.

9. The method of claim 8, further comprising performing at least one reduction step at the fractured bone on the basis of the set of malalignment parameters, if the deviations are not acceptable.

10. The method of claim 1, further comprising determining the imaging characteristics of the fluoroscope corresponding to the first and second set of fluoroscopic images.

11. The method of claim 10, further comprising determining calibration parameters of the fluoroscope.

12. The method of claim 1, further comprising obtaining a 3D representation of the contralateral bone from the first set of images, and obtaining the mirrored 3D representation from the 3D representation of the contralateral bone.

13. The method of claim 1, wherein the relative position further comprises a relative orientation.

14. The method of claim 1, further comprising the step of
defining a proximal configuration of the proximal bone fragment based on the transferred first set of 3D coordinates, and a distal configuration of the distal bone fragment based on the transferred second set of 3D coordinates,
wherein the defining step is performed based on the proximal and distal configurations.

15. The method of claim 1, wherein the moving step comprises translating at least one of the proximal and distal bone fragments toward the other of the proximal and distal bone fragments.

16. The method of claim 15, wherein the moving step comprises rotating at least one of the proximal and distal bone fragments relative to the other of the proximal and distal bone fragments.

17. The method of claim 1, wherein the moving step comprises rotating at least one of the proximal and distal bone fragments relative to the other of the proximal and distal bone fragments.

\* \* \* \* \*